United States Patent [19]

Thull et al.

[11] Patent Number: 5,074,881
[45] Date of Patent: Dec. 24, 1991

[54] HIP JOINT SOCKET FOR IMPLANTATION WITHOUT CEMENT INTO THE ACETABULUM OF THE HIP BONE

[76] Inventors: Roger Thull, Waldkugelweg 23, D-8700 Wuerzburg; Guenther Zeiler, Wallensteinstr. 30, D-8503 Altdorf, both of Fed. Rep. of Germany

[21] Appl. No.: 494,453

[22] Filed: Mar. 16, 1990

[30] Foreign Application Priority Data

Mar. 17, 1989 [DE] Fed. Rep. of Germany ... 8903328[U]

[51] Int. Cl.⁵ .............................................. A61F 2/32
[52] U.S. Cl. ...................................................... 623/22
[58] Field of Search ........................ 623/16, 18, 20, 22, 623/23

[56] References Cited

U.S. PATENT DOCUMENTS 4,792,337 12/1988 Muller .................................. 623/22
4,834,759 5/1989 Spotorno et al. .................... 623/22
4,961,748 10/1990 Frey et al. ............................ 623/22

FOREIGN PATENT DOCUMENTS 169978 1/1989 European Pat. Off. .
2807289 8/1979 Fed. Rep. of Germany ........ 623/22

OTHER PUBLICATIONS

Medizintechnik-Rehabilitation, a prospectus of the Protek AG company.

*Primary Examiner*—David J. Isabella
*Attorney, Agent, or Firm*—Sixbey, Friedman, Leedom & Ferguson

[57] ABSTRACT

A hip joint socket for implantation without cement into the acetabulum of the hip bone, consisting of an elastic socket support, which has the shape of an essentiallly hemispherical shell and can be inserted in an interlocking manner into the correspondingly prepared acetabulum bed. The socket support is formed so that after its implantation it quicklly grows together with the hip bone, and, even with considerable stress, relative movement between the socket support and the acetabulum is prevented. This is attained by constructing the socket support so that it exhibits its greatest stiffness in cranial portion in the implanted state, while in the downward (caudal) direction the elasticity of socket support increases. The wall thickness of socket support is greatest in cranial portion and decreases in the direction toward caudal portion. In the elastic caudal portion of the socket support, two or more notches are provided that run parallel or substantially parallel to the equatorial plane with increased elasticity at different distances from the equatorial plane.

20 Claims, 3 Drawing Sheets

HIP JOINT SOCKET FOR IMPLANTATION WITHOUT CEMENT INTO THE ACETABULUM OF THE HIP BONE

TECHNICAL FIELD

The invention relates to a hip joint socket for implantation without cement into the acetabulum of the hip bone, consisting of an elastic socket support which exhibits the shape of an essentially hemispherical shell and which can be inserted in an interlocking manner into the acetabulum bed.

BACKGROUND OF THE INVENTION

A hip joint socket is the part of a hip joint prothesis system that is to be implanted into the hip bone of a patient, while the other part, consisting of a shaft and a neck piece bearing a spherical head, represents the part of this system to be implanted into the femur.

Such a hip joint socket frequently comprises a socket support made of metal which can be inserted into the correspondingly prepared acetabulum bed and be mounted there, as well as an inner socket made of plastic that can be inserted in an interlocking manner into the concave side of the socket support, and the concave side of the inner socket serves as a bearing for the spherical head of the hip joint prothesis.

A prospectus of the PROTEK AG Company, CH-3001 Bern, 1988/1 edition and EPO 169978B1 disclose a full hip prothesis system CLS without cement. In this system, the socket support consists of a rotationally symmetrical hemispherical shell including six radial notches, which penetrate most of the hemispherical shell to form six tabs. The tabs become wider toward the equator and are arranged in the shape of a star. On these tabs are located outwardly directed anchoring points placed radially in three rows.

To implant this socket support into the prepared acetabulum bed the elastic tabs are pressed together with a collet chuck and the socket support is positioned in the acetabulum. When the collet chuck is released, the areas of the socket support near the equator are pressed against the bone by the tension acting radially outward. With an expansion cone or with a plastic inner socket, the socket support is then spread so that the anchoring points can be pressed into the bone and thus produce a stable primary anchoring of the socket support.

A secondary anchoring is made possible by the growth of bone substance on protrusions of the outer surface of the socket support, which are designed as firmly anchored fringes without undercut.

The elasticity of this socket support is present only to facilitate its insertion into the acetabulum With the collet chuck. To achieve this elasticity, moreover, the wall thickness in the transition area between the anchoring points and the pole is very thin. However, since the axis of symmetry of this implanted socket support is inclined at an angle of approximately 45° to the axis of the patient's body, the forces transmitted from the spherical head of the joint prosthesis to the socket support in a patient who is standing are the greatest precisely where the socket support has its weakest places Thus, the danger exists that the socket support will become deformed, so that even under the normal stress of walking, for example, both the primary and the secondary anchoring can become loose. In any case, a solid connection to the bone may not be formed.

A further disadvantage is that this known socket support is both difficult and expensive to produce, particularly because of the numerous anchoring points which must be individually machined.

SUMMARY OF THE INVENTION

Thus the object of the invention is to provide a hip joint socket for a hip joint prosthesis system to be implanted into the hip bone of a patient that can be machined in an inexpensive way by simple turning and milling processes, which after its implantation quickly grows together with the hip bone and, even under considerable stress, prevents relative movement between the socket support and the acetabulum.

This object is obtained by providing a hip joint socket for implantation without cement into the acetabulum of the hip bone consisting of an elastic socket support shaped like a substantially hemispherical shell that can be inserted in an interlocking manner into the prepared acetabulum bed. The implanted socket support exhibits its greatest stiffness in an upward or cranial direction and increased elasticity in a downward or caudal direction because the thickness of the socket support wall is the greatest in the cranial upper portion and decreases in the caudal lower portion. Two or more notches or cutouts that are substantially parallel to the equatorial plane of the support socket are provided at different distances from the equatorial plane.

The socket support is made of metal and is designed to have a solid upper portion which corresponds to the outer surface of a quarter sphere, while the remaining lower quarter sphere portion is designed to be as elastic as possible, with the flexibility depending on the location.

According to a further development of the invention, the notches aligned parallel or substantially parallel to the equatorial plane extend to or near the axis of symmetry or even slightly beyond it at different distances from the equatorial plane, and one or more links are formed which are divided into several link segments by a radial notch. This configuration produces an elastic portion of the socket support with highly elastic link segments whose elasticity can be controlled by the number of notches and by the widths of the link segments.

It is particularly advantageous if the thickness of the link segments on both sides of the radial notch increases up to the end of the link segments and preferably if the thickness increases continuously. This permits the elasticity of the link segment to be adapted to specific needs. In particular, a uniform bending stress of the link segments can be set over their equatorial span.

To facilitate the production of the hip joint sockets of the present invention on automatic lathes, a further configuration of the invention has an inner surface and an outer surface of the socket support which exhibit the shape of hemispheres with equatorial planes covering one another, yet with differing diameters and with axes of symmetry displaced parallel to one another. This hemisphere shape further avoids any kind of edge, which often occurs with a cylindrical or conical outer socket support shape. Edges present a constant danger, because of the high pressures acting in these places on the bone, of injuring the supporting bone structures or of weakening them by bone transformation.

Three notches are advantageous for attaining a flexibility corresponding to that of the natural joint. The links that result between these notches at the same time serve as fixing elements for the bone growing into the socket support. This produces both a mechanically solid anchoring and also an elastic anchoring of the bone in the elastic socket support.

Finally, according to a further configuration of the invention, the socket support can include an inner segment made of plastic, preferably polyethylene, inserted into the socket support in an interlocking manner so that it is impeded from pivoting around the axes located in the equatorial plane by a collar supported on the edge of the socket support.

Further advantageous characteristics of the present invention are explained below in greater detail.

DETAILED DESCRIPTION OF THE PREFERRED EMBODIMENT

Figure 1:
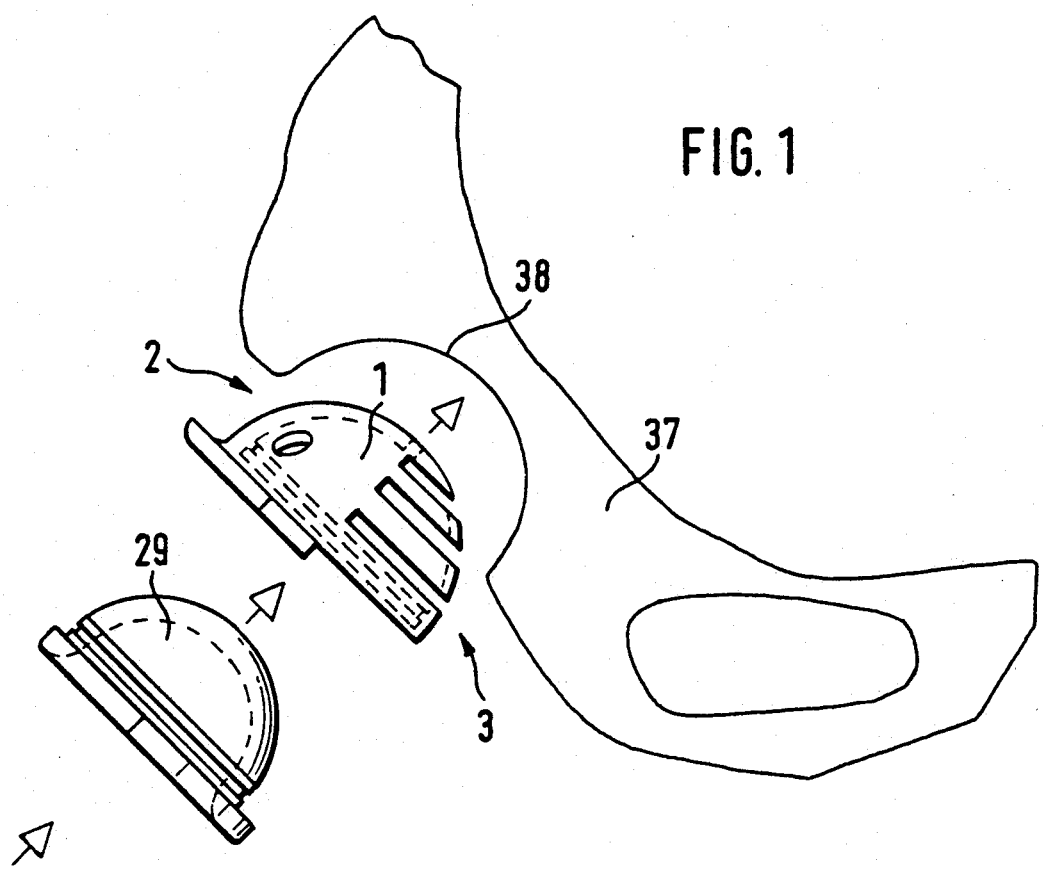
FIG. 1 shows an exploded representation of a hip joint socket in its working position.
Figure 6:
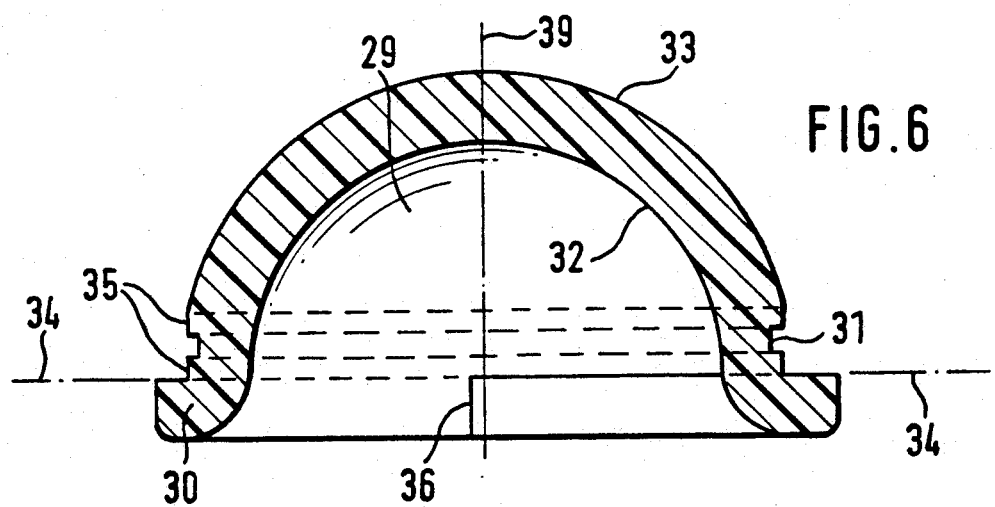
FIG. 6 shows a side section through an inner socket.
Figure 7:
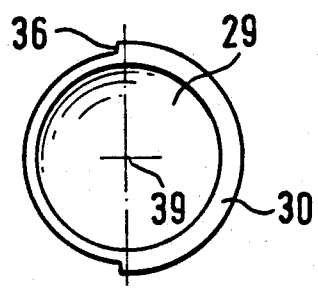
FIG. 7 shows the top view of the inner socket according to FIG. 5 on a reduced scale.

FIG. 1 shows hip bone 37 with acetabulum 38. The term "acetabulum" designates the natural hip joint in this application. The elastic socket support 1 of the present invention can be inserted in an interlocking manner into the correspondingly prepared, preferably milled, acetabulum bed. Into this socket support 1, which is made of metal, preferably titanium, an inner socket 29, made of plastic, preferably polyethylene, can be inserted and fastened into socket support 1 after its implantation.

As can be seen from FIG. 1, cranial portion 2 and caudal portion 3 of support 1 comprise quarter portions of a hemisphere. When the socket support 1 is implanted, it exhibits its greatest stiffness in cranial portion 2 in an upward or cranial direction, while in the lower or caudal direction of caudal portion 3, the elasticity of socket support 1 increases. This is attained by making the wall thickness of socket support 1 greatest in cranial portion 2, for example 3.5 mm, and decreasing the wall thickness in the direction toward caudal portion 3, so that the smallest wall thickness is about 1.5 mm. Moreover, the elasticity of socket support 1 in the portion with increased elasticity is also controlled by providing at different distances from equatorial plane 6 (FIG. 2) two or more notches or cutouts 11, 12, 13 (FIG. 2 and 3) running parallel or substantially parallel to equatorial plane 6.

In FIGS. 2 to 5 further details of the socket support 1 are represented.

The inner surface and the outer surface of socket support 1 essentially exhibit the shape of two hemispheres 4, 5 with equatorial planes 6 covering one another, yet with differing diameters and with axes of symmetry 7, 8 displaced parallel to one another.

Figure 2:
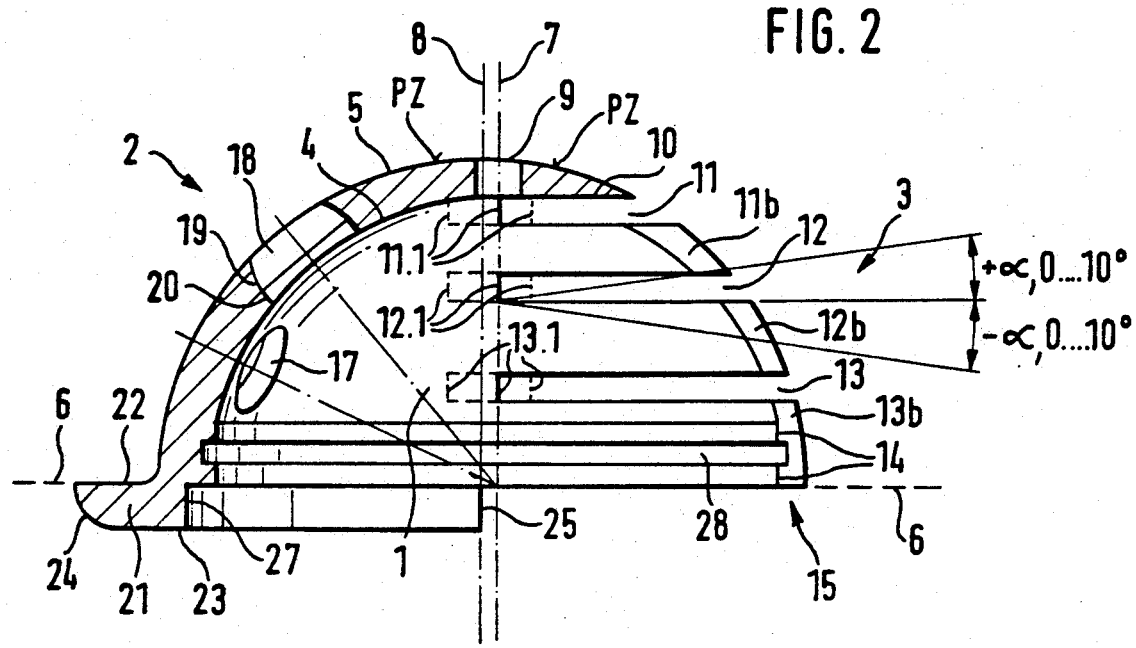
FIG. 2 shows a side view of the socket support according to section I—I of FIG. 4.

In the part of socket support 1 located below (represented in FIG. 2 on the right) axis of symmetry 7 of inner hemisphere 4 at different distances from equatorial plane 6, there are provided three notches 11, 12, 13 running parallel to equatorial plane 6. In the embodiment shown, these notches extend to the plane running through the axis of symmetry 7 of inner hemisphere 4, so that, as shown in FIG. 2, inner delimitation edges 11.1, 12.1, 13.1 of notches 11, 12, 13 coincide with this plane. However inner delimitation edges 11.1, 12.1, 13.1 can also run behind the axial plane, as represented in FIG. 2 with a broken line, or in front of this plane, as represented in FIG. 2 by the dotted line.

Figure 3:
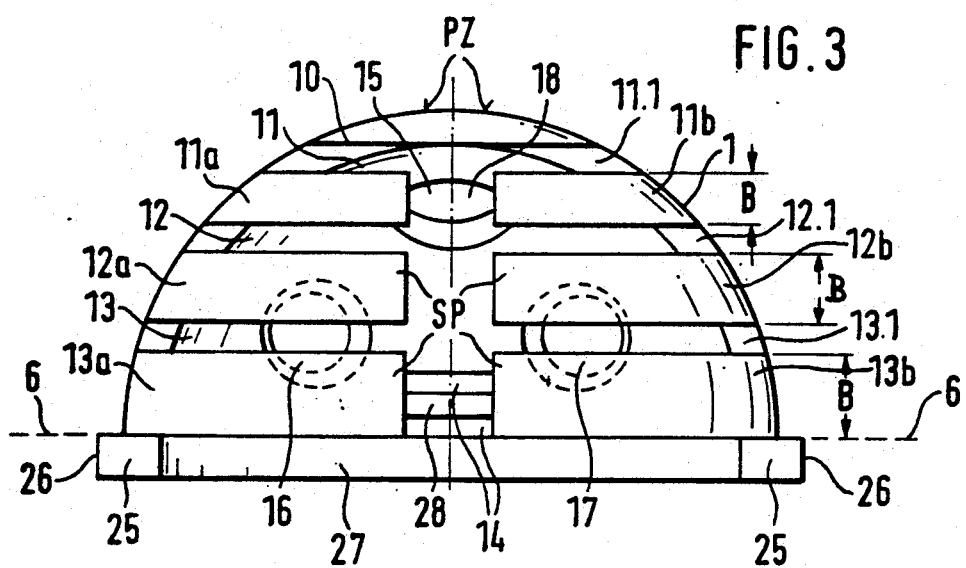
FIG. 3 shows a rear view of this socket support.

Preferably notches 11, 12, 13 have a width of 1.5 mm to 2.5 mm, and their intervals, namely width B of links SP, that are thereby formed increase relative to one another in the direction of equatorial plane 6 (FIG. 3). Upper segment surface 10 of top notch 11 is placed so that it touches inner hemisphere surface 4 in socket center PZ tangentially. More or fewer than three notches 11, 12, 13 running parallel to one another can also be provided. Additionally, it can be advantageous in different cases or applications to have notches 11, 12, 13 end before axis of symmetry 7 or to extend slightly beyond axis of symmetry 7, preferably, several millimeters up to about 1.5 cm. In the first case the elasticity of socket support 1 is reduced, while in the second case it is increased.

Notches 11, 12, 13 run preferably parallel to equatorial plane 6 (FIG. 2 and 3). However, the inclination of notches 11, 12, 13 to equatorial plane 6, preferably up to ±5°, maximally up to ±10°, may also be modified within the scope of the invention. These configurations of the invention are indicated in FIG. 2 by angles + and − drawn in.

Figure 4:
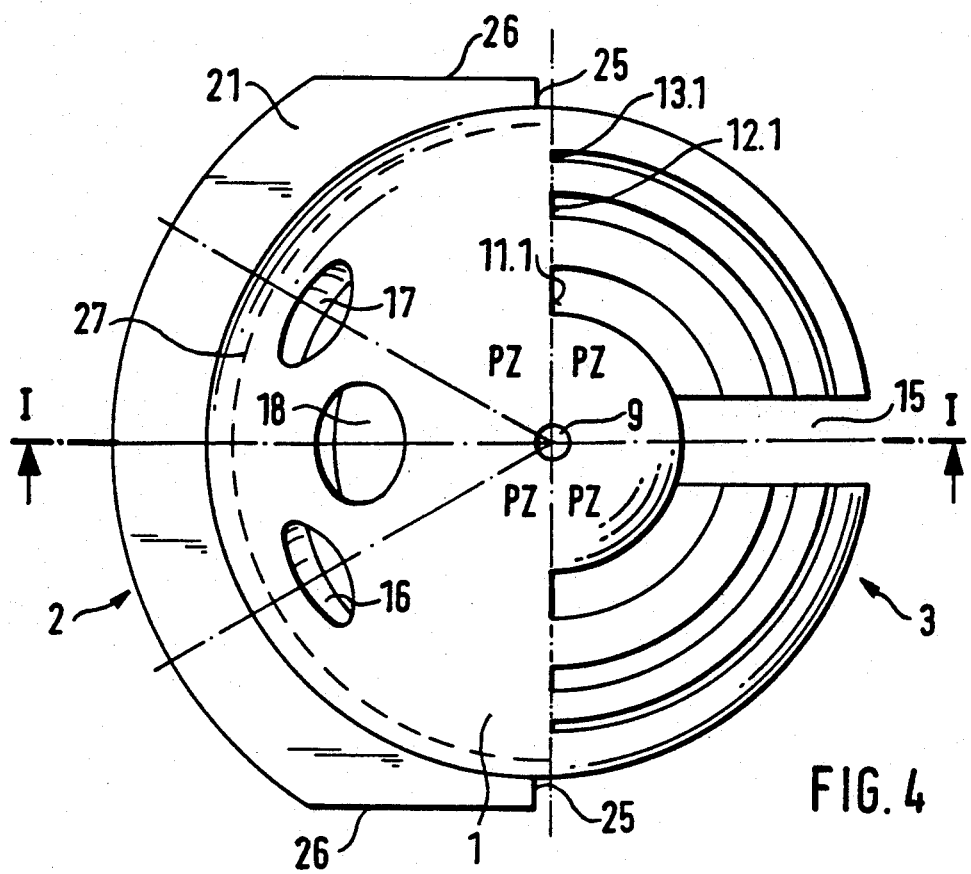
FIG. 4 shows a top view of this socket support.
Figure 5:
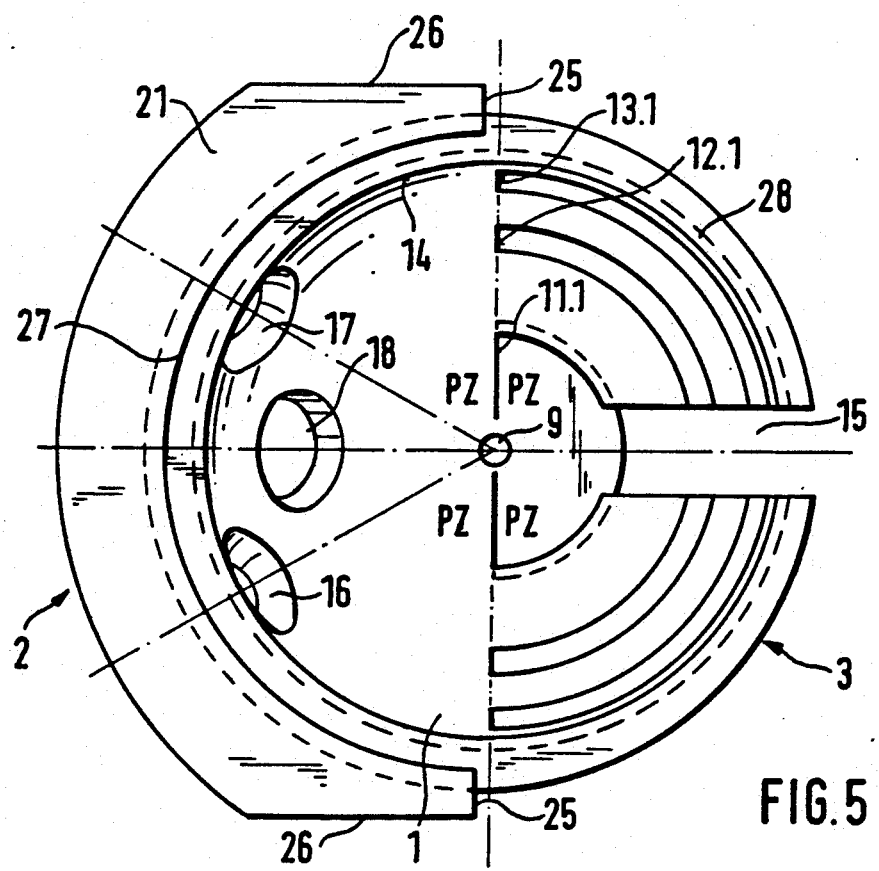
FIG. 5 shows a bottom view of this socket support.

It is also useful that radial notch 15 extend only to the top notch 11 parallel to equatorial plane 6. The socket center PZ will then form a closed surface without notches in the increased elasticity porition of socket support 1, as FIG. 4 shows.

In cranial portion 2 (FIG. 2 to the left) of socket support 1, three openings 16, 17, 18 are provided with countersunk heads for receiving fastening screws. The primary anchoring of socket support 1 in hip bone 37 is produced by these fastening screws. Two of the openings 16, 17 are placed near the edge at an angle of 25° and additional opening 18 is placed far from the edge at an angle of 50° above equatorial plane 6. The centers of both openings 16, 17 are displaced parallel to equatorial plane 6 at 30° to both sides in relation to opening 18. Openings 16, 17, and 18 are hemispherically shaped in outer area 19 and cylindrically shaped in adjoining inward area 20, with a diameter of 8 mm.

The primary anchoring of socket support 1 in hip bone 37 is produced preferably by three bone screws, whose screw-in direction can be varied by the construction of openings 16, 17, 18 described above within a cone with an aperture angle of 10°. Thus, these screws can be positioned into hip bone 37 both according to the anatomical proportions of the patient and in the direction of the force flow.

On the part of socket support 1 located above (in FIG. 2 left) the axis of symmetry 8 of outer hemisphere 5, a collar 21 extending outward from the edge is provided. The upper side 22 of the collar 21 is coplanar with equatorial plane 6, and the bottom side 23 of the collar 21 is parallel to and below equatorial plane 6. The bottom side 23 is rounded at 24 on the outer edge, which meets upper side 22 at a right angle. In this case, the radius of curvature of rounded portion 24 is equal to the thickness of collar 21, preferably 3 mm, which has a width of about 6 mm. The transition from upper side 22 of collar 21 to outer hemisphere 5 is rounded to have a radius of curvature of about 1.5 mm.

Collar 21 extends on both sides to the plane running through axis of symmetry 8 of outer hemisphere 5 and there forms radial end surfaces 25. Further, it is delimited in the area of these end surfaces 25 by two parallel surfaces 26, whose distance from one another is slightly greater, preferably by 4 mm, than the diameter of socket support 1. However, this distance can also be equal to the diameter of socket support 1.

Collar 21 is limited toward the inside by the generated surface of cylinder 27, whose axis of symmetry coincides with axis of symmetry 7 of inner hemisphere 4 and whose diameter is about 4 mm greater than the diameter of inner hemisphere 4.

The inner surface of socket support 1 near equatorial plane 6 changes from the shape of inner hemisphere 4 into the shape of a cylinder 14 with a height of 4.5 mm, and its axis of symmetry coincides with axis of symmetry 7 of inner hemisphere 4. The cylinder includes a groove 28 with a depth of 0.8 mm and a width of 1.4 mm which rotates at a slight distance of about 1.5 mm from equatorial plane 6. A spring wire can be inserted firmly into the groove 28 to secure inner socket 29. Other mechanical catches, for example bayonet locks and the like, could also be used.

Socket support 1 also includes opening 9, which is preferably cylindrical and located symmetrically to the axis of symmetry 7 of inner hemisphere 4. The opening 9 has a diameter of about 3 mm, and serves as a centering aid or for preliminary fixing when the socket support 1 is inserted into hip bone 37.

As already mentioned, socket support 1 is preferably made of titanium. The socket support 1 may also be made of titanium alloys or other metals that the body can tolerate.

Cranial portion 2, which extends from opening 9 on the axis of symmetry 7 to collar 21, as well as upper side 22 of collar 21 are preferably coated with titanium powder or with hydroxy apatite. They can also be coated with titanium tantalum oxide, particularly by high frequency plasma fastening. However, preferably these surfaces are roughened mechanically by sand blasting or by other mechanical methods, like the PVD (Physical Vapor Deposition) process, and provided with a "bone compatible" hard material coating made of oxides, nitrides or oxynitrides of so-called "valve metals." In addition, mixed metal oxide coatings of titanium-zirconium, titanium-niobium, titanium-tantalum, titanium-hafnium, titanium-tungsten, titanium-tantalum zirconium, titanium-tantalum niobium, titanium-tantalum hafnium, zirconium-niobium, niobium-hafnium or tantalum-zirconium can be used.

The advantage of roughening the surface coating of socket support 1 lies particularly in the fact that roughness prevents relative movement between socket support 1 and the growing bone In contrast to powder coatings, the danger of subsequent abrasion because of this relative movement does not exist. Rather, in subsequent coating of the roughened surface of the socket support with hard metal, the structure of the coating remains essentially preserved.

Socket support 1 is preferably made of solid material with diameters of 44 mm, 46 mm, 48 mm, 50 mm, 52 mm, 54 mm and 56 mm by machining operations.

FIG. 8 shows in lateral section an inner socket 29 made of plastic, preferably polyethylene, which can be inserted in an interlocking manner into socket support 1 and whose inner surface and outer surface exhibit the shape of concentric hemispheres 32, 33 with differing diameters, and the outer surface of inner socket 29 near equatorial plane 34 changes from the shape of the outer hemisphere 33 into the shape of a cylinder 35, which corresponds with the corresponding inner surface of socket support 1.

On equatorial plane 34 of hemispheres 32, 33 there is an adjoining collar 30, which is supported by the edge of socket support 1, if the inner socket 29 is inserted into the socket support 1 This collar 30 prevents the inner socket 29 from pivoting around the axes located in equatorial plane 34.

Collar 30 of inner socket 29 includes a step 38 approximately in the middle, which adjoins radial end surfaces 25 of collar 21 of socket support 1 and in this way prevents the inner socket 29 from rotating around its axis of symmetry 39.

The inner surface and outer surface of inner socket 29 have the shape of concentric hemispheres 32, 33 with differing diameters, and the outer surface of inner socket 29 near equatorial plane 34 changes from the shape of outer hemisphere 33 into the shape of cylinder 35 which corresponds to the corresponding inner surface of socket support 1.

In outer hemisphere 33 near equatorial plane 34, a circumferential groove 31 is provided which corresponds to groove 28 of socket support 1. Into both grooves 28 and 31 a spring wire or another mechanical stop element can be inserted to prevent inner socket 29 from falling out of socket support 1.

While we have shown and described a single embodiment in accordance with the present invention, it is understood that the same is not limited thereto, but is susceptible of numerous changes and modifications as known to those skilled in the art, and we, therefore, do not wish to be limited to the details shown and described herein, but intend to cover all such changes and modifications as are encompassed by the scope of the appended claims.

We claim:

1. A hip joint socket for implantation without cement into the acetabulum of the hip bone, consisting of a hemispherically shaped elastic socket support divided into a cranial portion and a caudal portion forming respective halves of said socket support, said shell having an equatorial plane and an axis of symmetry, wherein:

said shell can be inserted in an interlocking manner into a prepared acetabulum bed so that the implanted socket support exhibits its greatest stiffness in the cranial portion, while the elasticity of the socket support increases in a caudal direction toward the caudal portion;

the wall thickness of the socket support is greatest in the cranial portion and decreases in the direction of the caudal portion;

and the caudal portion of said socket support further includes at least two cutouts extending circumferentially about the socket forming circumferential fingers aligned substantially parallel to the equatorial plane.

2. A hip joint socket according to claim 1, wherein said cutouts extend varying distances relative to the socket support axis of symmetry and are spaced at varying distances from the equatorial plane to form one or more links, and said links are divided by a radial cutout into link segments.

3. A hip joint socket according to claim 2, wherein the thickness of each of said link segments on both sides of the radial cutout increases from one end to the other end of said link segments.

4. A hip joint socket according to claim 1, wherein said cutouts are inclined relative to the equatorial plane, and the inclination of said cutouts is up to a maximum of ±10° to the equatorial plane.

5. A hip joint socket according to claim 7, wherein said socket support has an inner surface and an outer surface, and both the inner surface and the outer surface of the socket support are shaped like hemispheres with co-planar equatorial planes, wherein the diameters of each hemisphere are different and the axes of symmetry of one hemisphere is displaced parallel to the other hemisphere.

6. A hip joint socket according to claim 2, wherein the width of each of said link segments increases in the direction toward the socket support equatorial plane.

7. A hip joint socket according to claim 1, wherein the cutout farthest from the socket support equatorial plane includes an upper cut edge that tangentially touches the inner surface hemisphere in the center of the socket.

8. A hip joint socket according to claim 1, wherein a radial cutout extends only to a parallel cutout farthest from the socket support equatorial plane, thereby forming in the center of the socket a closed surface without cutouts but having increased elasticity.

9. A hip joint socket according to claim 1, wherein said socket support further includes a collar extending outwardly from an edge of the socket support and the above the axis of symmetry of an outer hemispherical surface of the socket support.

10. A hip joint socket according to claim 9, wherein said collar includes radial end surfaces and is delimited in the area of the radial end surfaces by two parallel surfaces whose distance from one another is equal to or only slightly greater than the outer diameter of the socket support.

11. A hip joint socket according to claim 7, wherein the shape of an inner surface of the socket support near the socket support equatorial plane changes from a hemisphere into a cylinder having an axis of symmetry coincident With the axis of symmetry of the inner surface.

12. A hip joint socket according to claim 7, wherein an inner surface of the socket support includes a circumferential groove spaced from the . equatorial plane.

13. A hip joint socket according to claim 1, wherein the socket support further includes an opening symmetrical to the axis of symmetry of an inner hemispherical surface having a diameter up to about 3 mm for temporarily fastening the socket support in the acetabulum bed.

14. A hip joint socket according to claim 1, wherein the socket support is made of a metal selected from the group consisting of titanium, titanium alloys and metals tolerated by the human body.

15. A hip joint socket according to claim 14, wherein the surface of the socket support cranial portion is coated with a coating selected from the group consisting of the oxides, nitrides and oxynitrides of titanium-zirconium, titanium-niobium, titanium-tantalum, titanium-hafnium, titanium-tungsten, titanium-tantalum-zirconium, titanium-tantalum-niobium, titanium-tantalum-hafnium, zirconium-niobium, niobium-hafnium and tantalum-zirconium.

16. A hip joint socket according to claim 1, wherein the socket support is formed from solid material by a milling operation.

17. A hip joint socket according to claim 1, further including an inner socket inserted in an interlocking manner into the socket support so that it is prevented from pivoting around axes located in the equatorial plane by a collar supported by the edge of the socket support.

18. A hip joint socket according to claim 17, wherein said inner socket is formed of plastic.

19. A hip joint socket according to claim 2, wherein the thickness of each of said link segments on both sides of the radial cutout increases continuously from one end to the other end of said link segments.

20. A hip joint socket according to claim 1, wherein said circumferential fingers are aligned parallel to the equatorial plane.

* * * * *